US009056000B2

(12) United States Patent
Luo et al.

(10) Patent No.: US 9,056,000 B2
(45) Date of Patent: Jun. 16, 2015

(54) FLEXIBLE STENT-GRAFT

(75) Inventors: Qiyi Luo, Shanghai (CN); Honglin Nie, Shanghai (CN); Qing Zhu, Shanghai (CN); Weiwen Sheng, Shanghai (CN); Fengliang Zhao, Shanghai (CN); Hui He, Shanghai (CN); Jie Li, Shanghai (CN); Yan-bin Gao, Shanghai (CN)

(73) Assignee: MicroPort Endovascular (Shanghai) Co., Ltd., Shanghai (CN)

( * ) Notice: Subject to any disclaimer, the term of this patent is extended or adjusted under 35 U.S.C. 154(b) by 1589 days.

(21) Appl. No.: 11/572,908

(22) PCT Filed: May 23, 2006

(86) PCT No.: PCT/CN2006/001068
§ 371 (c)(1),
(2), (4) Date: Nov. 1, 2007

(87) PCT Pub. No.: WO2006/125382
PCT Pub. Date: Nov. 30, 2006

(65) Prior Publication Data
US 2008/0195191 A1 Aug. 14, 2008

(30) Foreign Application Priority Data
May 24, 2005 (CN) .......................... 2005 2 0041828

(51) Int. Cl.
*A61F 2/06* (2013.01)
*A61F 2/07* (2013.01)
*A61F 2/82* (2013.01)
*A61F 2/89* (2013.01)

(52) U.S. Cl.
CPC ............. *A61F 2/07* (2013.01); *A61F 2002/067* (2013.01); *A61F 2002/075* (2013.01); *A61F 2250/0039* (2013.01); *A61F 2/89* (2013.01); *A61F 2230/0067* (2013.01)

(58) Field of Classification Search
CPC ............. A61F 2/06; A61F 2/86; A61F 2/856; A61F 2002/072; A61F 2002/823; A61F 2/88; A61F 2/90
USPC ............ 623/1.13, 1.15, 1.37, 1.16, 1.22, 1.35
See application file for complete search history.

(56) References Cited

U.S. PATENT DOCUMENTS

| | | | | |
|---|---|---|---|---|
| 5,800,515 A * | 9/1998 | Nadal et al. | ................... | 623/1.15 |
| 6,027,525 A * | 2/2000 | Suh et al. | ......................... | 623/1.1 |
| 6,648,913 B1 * | 11/2003 | Yee et al. | ...................... | 623/1.35 |
| 6,673,107 B1 * | 1/2004 | Brandt et al. | ................ | 623/1.35 |
| 6,945,992 B2 * | 9/2005 | Goodson et al. | ............. | 623/1.13 |
| 7,004,968 B2 * | 2/2006 | Lootz et al. | .................. | 623/1.15 |
| 7,615,072 B2 * | 11/2009 | Rust et al. | ..................... | 623/1.36 |
| 8,163,006 B2 * | 4/2012 | Feller et al. | .................. | 623/1.35 |

(Continued)

*Primary Examiner* — Thomas J Sweet
*Assistant Examiner* — Seema Mathew
(74) *Attorney, Agent, or Firm* — K. David Crockett, Esq.; Niky Economy Syrengelas, Esq.; Crockett & Crockett, PC

(57) ABSTRACT

A stent graft (5) comprises a tubular graft member (4), and a plurality of sloping stent members (3) substantially coaxial with and coupled to the tubular graft member (4). Each of the sloping stent members (3) comprises multiple uneven apexes characterizing a round tubular configuration with a distal end and a proximal end disposed about a longitudinal axis. The distal apexes of the sloping stent member (3) are arranged in substantially the same plane substantially horizontal to the longitudinal axis of the sloping stent member and the proximal apexes are arranged in a sloping plane oblique to the longitudinal axis.

33 Claims, 7 Drawing Sheets

(56) References Cited

U.S. PATENT DOCUMENTS

| | | | | |
|---|---|---|---|---|
| 8,226,703 B2* | 7/2012 | Caldarise et al. | | 623/1.13 |
| 8,425,585 B2* | 4/2013 | Melsheimer et al. | | 623/1.15 |
| 8,623,065 B2* | 1/2014 | Lau et al. | | 623/1.13 |
| 8,641,753 B2* | 2/2014 | MacAtangay et al. | | 623/1.13 |
| 8,663,309 B2* | 3/2014 | Chobotov | | 623/1.13 |
| 8,702,787 B2* | 4/2014 | Arbefeuille | | 623/1.15 |
| 8,709,068 B2* | 4/2014 | Shalev et al. | | 623/1.35 |
| 8,728,145 B2* | 5/2014 | Chuter et al. | | 623/1.13 |
| 8,728,148 B2* | 5/2014 | Roeder et al. | | 623/1.23 |
| 2002/0091439 A1* | 7/2002 | Baker et al. | | 623/1.36 |
| 2002/0177890 A1* | 11/2002 | Lenker | | 623/1.12 |
| 2003/0181969 A1* | 9/2003 | Kugler et al. | | 623/1.13 |
| 2004/0034402 A1* | 2/2004 | Bales et al. | | 623/1.2 |
| 2004/0193245 A1* | 9/2004 | Deem et al. | | 623/1.13 |
| 2004/0215319 A1* | 10/2004 | Berra et al. | | 623/1.13 |
| 2004/0215326 A1* | 10/2004 | Goodson et al. | | 623/1.16 |
| 2005/0033410 A1* | 2/2005 | Hogendijk et al. | | 623/1.15 |
| 2005/0154448 A1* | 7/2005 | Cully et al. | | 623/1.15 |
| 2005/0228484 A1* | 10/2005 | Stephens et al. | | 623/1.16 |
| 2005/0278017 A1* | 12/2005 | Gregorich | | 623/1.44 |
| 2006/0004436 A1* | 1/2006 | Amarant et al. | | 623/1.15 |
| 2006/0030926 A1* | 2/2006 | Berra | | 623/1.13 |
| 2006/0178733 A1* | 8/2006 | Pinchuk et al. | | 623/1.35 |
| 2006/0195172 A1* | 8/2006 | Luo et al. | | 623/1.13 |
| 2007/0055345 A1* | 3/2007 | Arbefeuille | | 623/1.13 |
| 2007/0088428 A1* | 4/2007 | Teichman | | 623/1.16 |
| 2007/0135889 A1* | 6/2007 | Moore et al. | | 623/1.13 |
| 2007/0225797 A1* | 9/2007 | Krivoruhko | | 623/1.35 |
| 2007/0233220 A1* | 10/2007 | Greenan | | 623/1.11 |
| 2008/0114441 A1* | 5/2008 | Rust et al. | | 623/1.13 |
| 2008/0114443 A1* | 5/2008 | Mitchell et al. | | 623/1.13 |
| 2008/0319535 A1* | 12/2008 | Craven et al. | | 623/1.22 |
| 2009/0082846 A1* | 3/2009 | Chobotov | | 623/1.13 |
| 2010/0152835 A1* | 6/2010 | Orr | | 623/1.15 |
| 2011/0022149 A1* | 1/2011 | Cox et al. | | 623/1.11 |
| 2011/0087318 A1* | 4/2011 | Daugherty et al. | | 623/1.13 |
| 2011/0166644 A1* | 7/2011 | Keeble et al. | | 623/1.24 |
| 2011/0218609 A1* | 9/2011 | Chobotov et al. | | 623/1.11 |
| 2012/0059452 A1* | 3/2012 | Boucher et al. | | 623/1.15 |
| 2012/0130478 A1* | 5/2012 | Shaw | | 623/1.35 |
| 2012/0259404 A1* | 10/2012 | Tieu et al. | | 623/1.15 |
| 2013/0131780 A1* | 5/2013 | Armstrong et al. | | 623/1.13 |
| 2013/0144373 A1* | 6/2013 | Shahriari | | 623/1.12 |
| 2013/0166010 A1* | 6/2013 | Vad | | 623/1.2 |
| 2013/0245745 A1* | 9/2013 | Vong et al. | | 623/1.12 |
| 2014/0088678 A1* | 3/2014 | Wainwright et al. | | 623/1.11 |
| 2014/0248418 A1* | 9/2014 | Eller et al. | | 427/2.25 |

* cited by examiner

FLEXIBLE STENT-GRAFT

FIELD OF THE INVENTION

The inventions described below relate the field of medical devices for use in treatment of vascular diseases. More specifically, the inventions described below relate to stent grafts for use in the treatment of thoracic aortic aneurysms and bifurcated stent grafts for use in treatment of abdominal aortic aneurysms.

BACKGROUND OF THE INVENTIONS

A stent graft is a medical device comprising a tube graft material supported by a metallic wire frame that may be used in the treatment of vascular diseases including aneurysms. Blood pressure within the diseased portion of the blood vessel can cause the aneurysm to rupture and hemorrhage. Stent-grafts can be used in the treatment of aneurysms, including thoracic aortic aneurysms and abdominal aortic aneurysms, by isolating the blood from the aneurysms. Typically, stents are deployed by placing them in a sheath of a delivery system and delivering the stent to the location where the aneurysm lies. After being deployed, the stent-graft expands and anchors onto healthy portions of the blood vessel on both ends adjoining the aneurysm. Once installed, blood flows through the tubular stent graft and the diseased portion of the blood vessel is isolated from the pressure of flowing blood.

A wide range of endovascular stent grafts have been developed that are adapted for temporary or permanent implantation within a body lumen including the abdominal aorta or thoracic aorta. These stent grafts provide uniquely beneficial structures that modify the mechanics of the targeted vessel wall. However, because conditions of weakened and diseased blood vessels differ greatly from patient to patient, existing stent-grafts have many drawbacks and may be restricted in their usefulness and applicability to certain procedures.

Many tubular stent grafts have been used in the treatment of aortic aneurysms, including abdominal aortic aneurysms and thoracic aortic aneurysms close to the aortic arch. The aortic arch comprises a sharp curve and disease and deformation of this blood vessel usually occurs close to the curved portion of the vessel. Because of the unique shape of the aortic arch, treatment of aneurysms in the aortic arch calls for flexibility and high performance in the stent-graft so that it can easily flex and adapt to the shape of the blood vessel. If the stent graft is not flexible, it cannot attach conformably to the wall of the blood vessel and may potentially kink. A kink in the stent graft will not only weaken the fixation of the stent graft to the vessel wall, but it may also raise the blood pressure within the graft due to the uneven or smaller inner diameter of the graft. High blood pressure in deployed stent grafts can lead to a higher flushing force of blood flow on the stent graft and a rise of the risk of stent graft migration as well. If the stent graft migrates within the arotic arch, it not only fails to isolate the blood from the aneurysm, but also may cover other branch vessels extending from the aorta. Covering the branch vessels in the aortic arch can lead to reduced blood flow to the rest of the body causing damage to nerves as well as vital organs of the patient and even death. Similar problems also exist when using bifurcated stent grafts in treatment of abdominal aortic aneurysms for the iliac arteries which also contain a sharp curve. Because of these issues, a more flexible stent graft is necessary in the treatment of aortic aneurysms.

The drawbacks in current stent graft designs also contribute to other complications in patients during and after stent graft treatment and placement. Endoleakage is a major complication of endovascular treatment of aortic aneurysms. Endoleakage is the persistence of blood flow into the aneurysm sac outside the stent graft. When endoleakage occurs, the aneurysm is not fully isolated from blood flow within the patient's blood vessel and risk of a potentially fatal rupture of the aneurysm remains. Most endoleakage occurs at the proximal portion of the stent graft once the stent graft is inserted into a patient. Improved deformability of the proximal end of stent grafts can prevent proximal endoleakage.

Present stent graft designs typically comprise an open stent that is not fully covered with graft material. Stents may comprise a series of waveforms or undulations having apexes. When aneurysm are located very close to an important branch vessel, the surgeon will position the proximal end of graft member with the open stent close to the distal end of the branch port and the open stent will cover the branch port in an effort to avoid occluding the branch. This method of stent graft placement does not occlude the branch port, improves the fixation of the stent graft to the vessel and strengthens the proximal radial supporting force of graft member.

While stent grafts with open stents have many advantages, use and placement of stent grafts having open stents is not without its risks. During the deployment of the stent graft when only the open stent is deployed from the deployment catheter sheath, the proximal apexes of the undulations of the open stent expand to their full diameter while the distal apexes of the undulations are still restricted. When the distal apexes are restricted, the expanded proximal apexes can overturn within the vessel. Overturning occurs when one or more complete undulations or one or more of the proximal apexes expand and turn backwards. During deployment of the stent graft, overturned apexes can stick to the wall of vessel. After full deployment of the stent graft, overturned undulations and apexes deform the proximal profile of the graft member and prevent the proximal end of the graft member from conformably attaching to the wall of vessel. A stent graft deformed in this manner increases the risk of proximal endoleakage as well as increases the risk of vessel rupture due to sticking of overturned apexes into the vessel wall.

One method used to reduce the potential of overturn of the apexes of the open stent, is to utilize longitudinally longer the open stents. Longer stents, however, not only cover the intended branch vessel, but also risk covering one more branch vessels not intended to be covered. Because stents are foreign objects within the human body, there is potential for the formation of blood clots known as thrombus on the surface of the stent wire. Since thrombus formation is unstable, there is a risk for it to be flushed away from the stent. When an open stent covers a branch, the thrombus may be flushed into the branch vessel and occlude some other smaller vessels of the branch. Occlusion of branch vessels can potentially be fatal to the patient. Less severe complications of open stents covering the port of the branch vessel include increased difficulty in future performance of minimally invasive surgery within the branch vessel due to vessel obstruction.

Other blood flow complications can occur during the deployment of bifurcated stents within patients. In bifurcated stent graft designs, two branches of varying lengths extended from a trunk portion of the graft. The longer branch is typically called the ipsilateral iliac branch and the shorter branch is typically called the contralateral iliac branch. During placement of a bifurcated stent graft, the distal part of ipsilateral branch is often positioned within the ipsilateral iliac artery and the entire contralateral iliac branch portion is positioned within the abdominal aorta. The abdominal aorta is the vessel that usually contains a large aneurysm sac or bubble. After the bifurcated stent graft is initially placed in the abdominal aorta, a branch stent graft extension positioned by a guide wire to be place in and joined to the bifurcated stent graft within the short branch, contralateral iliac branch.

The procedure placing the guiding wire into the contralateral iliac branch is difficult. The contralateral iliac branch typically has an inner diameter of about 10 to 14 mm. The abdominal aorta usually has an inner diameter of no more than 45 to 50 mm. Adding to the difficulties posed by the work space, blood flowing out from the short branch also works to prevent the guide wire from entering into the short branch. It often takes several attempts and 5 to 10 minutes to put the guide wire into the contralateral iliac branch, the short branch. This time accounts for ⅓ to ½ of the time a patient spends in surgery. What is needed is a stent and procedure that reduces the time a patient spends in surgery.

The disclosed invention provides for shortened surgery time and lessens the potential of injury to the patient from reduced blood supply during the operation.

SUMMARY

The present invention relates to an improved tubular stent graft and a bifurcated stent graft. The tubular stent graft comprises multiple sloping stent members, a mini-wave stent member, an open stent member and a tubular graft member and provides improved flexibility, enhanced fixation to the vessel wall, reduced endoleakage and reduced potential of overturns of the proximal apexes of the open stent member during stent graft deployment.

The sloping stent member comprises a wire having multiple uneven undulations or sine waveforms of differing heights characterized by apexes or crests and troughs. The wire is formed in a tubular or ring-like configuration about a longitudinal axis. The tubular configuration may be conical in shape with a progressively smaller inner diameter from the proximal end to the distal end of the sloping stent member. The distal apexes or troughs of the sloping stent member forming the distal circumference of the sloping stent member lie on the same plane approximately horizontal/perpendicular to the longitudinal axis. The proximal apexes or crests are arranged in a sloping plane that is oblique to the longitudinal axis making the wave heights progressively shorter. The proximal apex of the waveform with the highest wave height or of the undulation with the longest longitudinal length from the proximal apex to the distal apex shall be referred to as the high wave apex and the proximal apex having the shortest longitudinal length shall be referred to as the short wave apex.

The mini-wave stent member comprises a wire having multiple uneven undulations or sine waveforms of differing heights characterized by apexes or crests and troughs. The wire is formed in a tubular or ring-like configuration about a longitudinal axis. The distal apexes or troughs of the mini-wave stent forming the distal circumference of the mini-wave stent lie on the same plane approximately horizontal/perpendicular to the longitudinal axis. The proximal apexes or crests are arranged along two different planes approximately horizontal/perpendicular to the longitudinal axis providing the undulations or waveforms with two different heights. The proximal apexes of the waveforms with the highest wave heights or of the undulations with the longest longitudinal lengths from the proximal apexes to the distal apexes shall be referred to as the high wave apexes and the proximal apexes having the shortest longitudinal lengths shall be referred to as the short wave apexes. Preferably, one or two high wave apexes are disposed between every two short wave apexes. In contrast to the sloping stent member, the mini-wave stent member is made of thinner wire with smaller undulations or wave heights and more undulations and apexes. Typically, the number of apexes in the mini-wave stent member about double the number of apexes found in the sloping stent member.

The open stent member comprises a wire having multiple uneven undulations or sine waveforms of differing heights characterized by apexes or crests and troughs. The wire is formed in a tubular or ring-like configuration about a longitudinal axis. The distal apexes or troughs of the open stent member forming the distal circumference of the open stent lie on the same plane approximately horizontal/perpendicular to the longitudinal axis. The proximal apexes or crests are arranged along at least two different planes approximately horizontal/perpendicular to the longitudinal axis providing the undulations or waveforms with two or more different heights. The proximal apexes of the waveforms with the highest wave heights or of the undulations with the longest longitudinal lengths from the proximal apexes to the distal apexes shall be referred to as the high wave apexes and the proximal apexes having the shortest longitudinal lengths shall be referred to as the short wave apexes. Preferably, all the proximal apexes of the same height or longitudinal length are arranged together and adjacent to one another.

The stent graft comprises an open stent member, a mini-wave stent member and a plurality of sloping stent members placed in a series of neighboring adjacent instances and coupled in a substantially coaxial manner to a tubular graft member. The open stent member is coupled by its distal apexes to the proximal end of the graft member. The mini-wave stent member and the sloping stent members are coupled to the graft member distally from the open stent member. The sloping stent members are spaced longitudinally apart from one another.

Typically, a connecting bar couples and connects the proximal most stent member to the distal most stent member in the stent graft. The radial side of the stent graft where the connecting bar lies is referred to as the rigid side. In an alternative embodiment, a connecting bar may be individually placed between every two neighboring stent members connecting the two adjacent stent members together. In this design, all the connecting bars are arranged substantially coaxial along the same rigid side.

Sloping stent members are placed substantially coaxial to the longitudinal axis of the graft member in neighboring adjacent instances within the stent graft. The high wave apexes of the sloping stent members are positioned on the rigid side and the distal ends of each sloping stent member are directed towards the distal end of the stent graft. The short wave apexes of the sloping stent members are arranged on the same radial side of the circumference of the stent graft. This radial side is referred to as the flexible side of the stent graft. Because of the wedge shape of the sloping stent members, the distance between proximal apexes of each stent member and its neighboring stent member on the flexible side of the stent graft is greater than the distance between each stent member and its neighboring stent member on the rigid side. The open stent member is placed coaxially with the graft member having the short wave apexes on the rigid side. The mini-wave stent member is placed coaxially with the graft member and disposed between the open stent member and the proximal most sloping stent member. The proximal high wave apexes of the mini-wave stent member are substantially aligned with the proximal apexes of the open stent member. The proximal short wave apexes of the mini-wave stent member are substantially aligned with the distal apexes of said open stent member.

The bifurcated stent graft comprises a bifurcated graft member and a plurality of supporting stent members. The bifurcated stent graft provides improved flexibility in a long branch portion, enhanced fixation to the vessel wall, reduced endoleakage and ease of introducing a guiding wire into a short branch graft portion. The bifurcated tubular graft member has a trunk graft portion with two branch portions extending from its distal end. The first branch portion extending from the trunk portion is a long branch graft portion referred to as an ipsilateral iliac branch graft portion. The second branch portion is a short branch graft member referred to as a contralateral iliac branch graft portion. Extending from the shorter branch graft member is an umbrella-like or flared introducing graft portion having a larger distal diameter than the short branch graft member.

The supporting stent members in the bifurcated stent graft may include one or more mini-wave stent members, a plurality of sloping stent member and a plurality of uniform stent members. The mini-wave stent members and sloping stent members are of the same configuration as previously discussed. The uniform stent member comprises multiple even undulations and apexes defining a tubular configuration with the proximal apexes or crests lying in substantially the same plane and the distal apexes or troughs lying in substantially the same plane. The uniform stent has substantially the same longitudinal distance or wave height along the uniform stent member. A mini-wave stent member is disposed substantially coaxially with and coupled to the introducing graft portion. Another mini-wave stent member is also disposed substantially coaxially with and coupled to the proximal end of the trunk graft portion.

The long branch graft portion comprises a plurality of sloping stent members substantially coaxial with and coupled to the long branch graft portion. A connecting bar connecting the proximal most stent member to the distal most stent member within the long branch graft portion is disposed within the long branch graft portion. The high wave apexes of the sloping stent members within the long branch graft portion are positioned on the radial side where the connecting bar lies. The distal end of each sloping stent member is directed towards the distal end of the long branch graft portion. The connecting bar lies on the radial side closest to the short branch graft portion. This side is referred to as the rigid side of the long branch graft portion. As an alternative design to a single connecting bar, connecting bars may be individually disposed between and coupled to every two neighboring stent members connecting the two stent members together.

Stent members, including open stent members, sloping stent members, mini-wave stent members and uniform stent members may be manufactured from nitinol, cobalt chrome alloys (e.g. Elgiloy), stainless steel, titanium/platinum/tungsten alloys, or other biocompatible alloys. The stent members composing the stent graft, including the sloping stent members, mini-wave stent member and open stent member, may be made individually from different continuous wire or alternatively, made from a same single continuous wire. Stent members may be manufactured from alloy tubing by laser cutting, chemical etching or other machining and cutting techniques. All these stent members may be cut or manufactured individually or alternatively, cut or manufactured in successive turns from the same alloy tubing, with each stent member connected to the neighboring stent member(s).

The graft member may be manufactured from expanded polytetrafluorethylene (ePTFE), polyester fabric, polypropylene, microporous urethane, hexafluoropropylene, polyfluorocarbon, Polyamide, polyethylene terephthalate, nylon, lycra, or other suitable biocompatible material, or alternatively a multilayer liner or compounding material made from one or one more of these materials. Stent members may be coupled to the graft member by suturing, bonding, sintering, welding, melting or the like, or a combination of these methods.

DETAILED DESCRIPTION OF THE INVENTIONS

Figure 1:
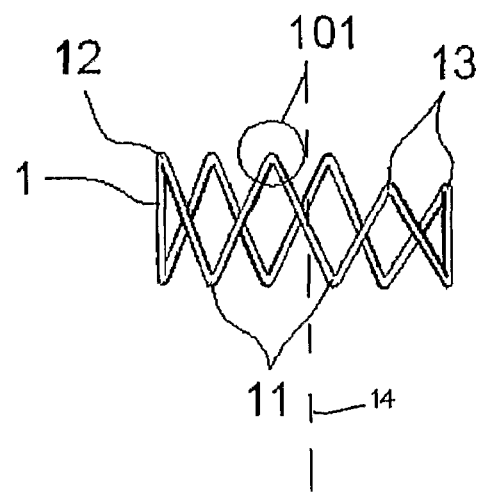
FIG. 1 illustrates an open stent member.

FIG. 1 illustrates an open stent member 1 formed from a single continuous wire and comprising multiple uneven undulations or sine waveforms of differing heights characterized by apexes or crests and troughs. The wire is formed in a tubular or ring-like configuration about a longitudinal axis. Apexes 11, 12, 13 characterize the tubular configuration. The distal apexes 11 or troughs of the open stent member 1 forming the distal circumference of the open stent lie on the same plane approximately horizontal/perpendicular to the longitudinal axis 14. The proximal apexes 12, 13 or crests are arranged along at least two different approximately horizontal/perpendicular to the longitudinal axis providing the undulations or waveforms with two or more different heights. The proximal apexes of the waveforms with the highest wave heights or of the undulations with the longest longitudinal lengths from the proximal apexes to the distal apexes are referred to as the high wave apexes 12 and the proximal apexes having the shortest longitudinal lengths are referred to as the short wave apexes 13. Preferably, all the proximal apexes of the same height or longitudinal length are arranged together and adjacent to one another. As illustrated in FIG. 1, all the short wave apexes 13 are arranged together in adjacent turns.

Figure 2:
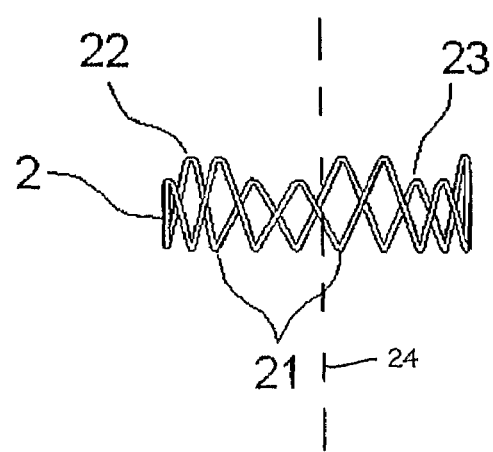
FIG. 2 illustrates a mini-stent member.

FIG. 2 illustrates a mini-stent member 2 that is formed from a single continuous wire. The mini-wave stent member comprises a wire having multiple uneven undulations or sine waveforms of differing heights characterized by apexes 21, 22, 23 or crests and troughs. The wire is formed in a tubular or ring-like configuration about a longitudinal axis 24. The tubular configuration may have a substantially uniform inner diameter or be conical in shape with a progressively smaller inner diameter from the proximal end to the distal end of the mini-stent member stent member. The distal apexes 21 or troughs of the mini-wave stent forming the distal circumference of the mini-wave stent 2 lie on the same plane approximately horizontal/perpendicular to the longitudinal axis. The proximal apexes 22, 23 or crests are arranged along two different planes approximately horizontal/perpendicular to the longitudinal axis providing the undulations or waveforms with two different heights. The proximal apexes of the waveforms with the highest wave heights or of the undulations with the longest longitudinal lengths from the proximal apexes to the distal apexes shall be referred to as the high wave apexes 22 and the proximal apexes having the shortest longitudinal lengths shall be referred to as the short wave apexes 23. Preferably, one or two high wave apexes are disposed between every two short wave apexes. In contrast to the sloping stent member, the mini-wave stent member is made of thinner wire with smaller undulations or wave heights and more undulations and apexes. Typically, the number of apexes in the mini-wave stent member about double the number of apexes found in the sloping stent member.

Figure 3:
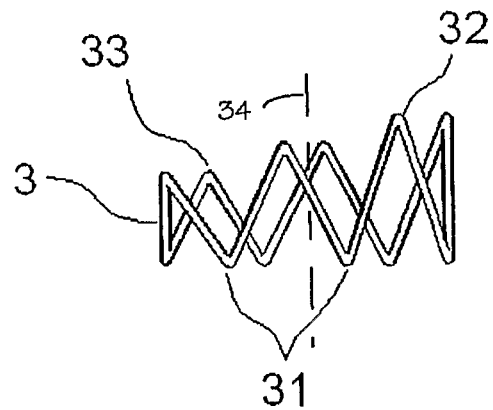
FIG. 3 illustrates a sloping stent member.

FIG. 3 illustrates a sloping stent member 3 that is formed from a single continuous wire. The sloping stent member comprises a wire having multiple uneven undulations or sine waveforms of differing heights characterized by apexes 31, 32, 33 or crests and troughs. The wire is formed in a tubular or ring-like configuration about a longitudinal axis 34. The tubular configuration may have a substantially uniform inner diameter or be conical in shape with a progressively smaller inner diameter from the proximal end to the distal end of the sloping stent member. The distal apexes 31 or troughs of the sloping stent member forming the distal circumference of the sloping stent member lie on the same plane approximately horizontal/perpendicular to the longitudinal axis. The proximal apexes or crests are arranged in a sloping plane that is oblique to the longitudinal axis making the wave heights progressively shorter. The proximal apex 32, 33 of the waveform with the highest wave height or of the undulation with the longest longitudinal length from the proximal apex to the distal apex shall be referred to as the high wave apex 32 and the proximal apex having the shortest longitudinal length shall be referred to as the short wave apex 33.

Figure 4:
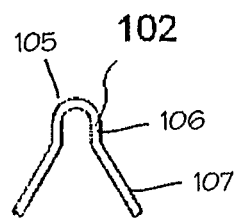
FIG. 4 illustrates an apex of a stent member having a modified arcuate shape.
Figure 5:
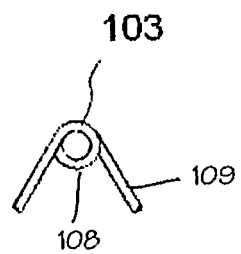
FIG. 5 illustrates an apex of a stent member having a coil shape.
Figure 6:
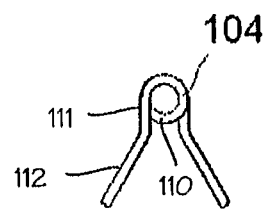
FIG. 6 illustrates an apex of a stent member having a modified arcuate shape with a coil.

FIG. 4, FIG. 5 and FIG. 6 illustrate alternative configurations of apexes 102, 103, 104 in stent members 1, 2, & 3. FIG. 4 illustrates an apex 102 having a modified arcuate shape. The modified arcuate shape comprises a stretched half circle 105 with straight segments 106 extending tangentially and vertically from the half circle. Angled segments 107 extend from the straight segments in an oblique manner to the vertical axis of the apex. FIG. 5 illustrates an apex 103 having a coil shape. The wire of the apex 103 is coiled to form a ring 108 having two angled segments 109 extending from the ring skewed to the vertical axis of the apex 103. FIG. 6 illustrates an apex 104 having modified arcuate shape with a coil. Here, the wire of the apex 104 is coiled to form a ring 110 having two straight segments 111 extending tangentially and vertically from the ring. Angled segments 112 extend from the straight segments skewed to the vertical axis of the apex 103.

Figure 7:
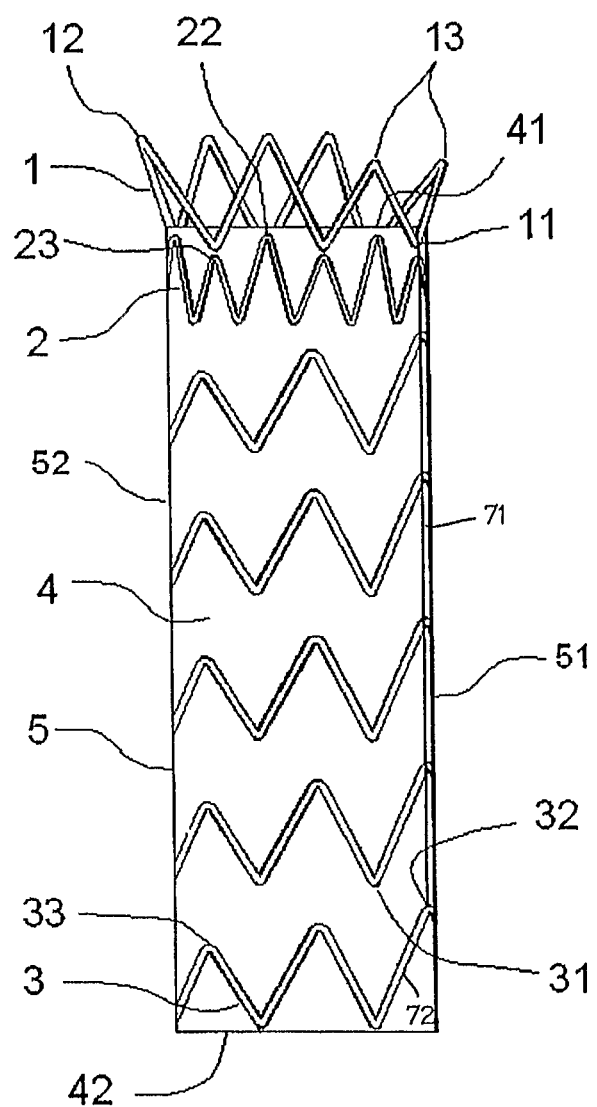
FIG. 7 illustrates a tubular stent graft.

FIG. 7 illustrates a tubular stent graft. The tubular stent graft 5 comprises an open stent member 1, a mini-wave stent member 2 and a plurality or sloping stent members 3 coupled in a series of successive neighboring instances from the proximal end to the distal end of the tubular graft member 4. The stent members may be disposed about the outer diameter of the graft member, within the inner diameter of the graft member or within the wall of the graft member.

The distal apexes 11 of the open stent member 1 are coupled to the proximal end 41 of the tubular graft member 4. The mini-wave stent member 2 is coupled to the tubular graft member 4 with the high wave apex 22 positioned close to the proximal end 41 of the tubular graft member 4 and between the distal apexes 11 of the open stent member 1. Multiple sloping stent members 3 are coupled to the tubular graft member 4 in a series of adjacent to one another. The sloping stent members are spaced apart in a uniform manner. The short wave apexes of the sloping stent members are arranged on the same radial side of the stent graft. This radial side is referred to as the flexible side 52 of the stent graft. The distance between proximal apexes of each stent member and its neighboring stent member on the flexible side of the stent graft is greater than the distances between the proximal apexes of neighboring stent members on the rigid side. The high wave apexes 32 of the sloping stent members are positioned on the same radial side, which is called the rigid side 51, aligned longitudinally with the short wave apex 13 of the open stent member 1. A longitudinal bar 71 connects the open stent member 1 and the distal most sloping stent member 72 on the rigid side 51 of the stent graft where the high wave apexes 32 of the sloping stent members 3 lie. Multiple radiopaque markers may be disposed within the tubular graft member 5.

All stent members, including the open stent member 1, the mini-wave stent member 2 and the sloping stent member 3, are made of biocompatible material, such as nitinol, cobalt chrome alloys (e.g. Elgiloy), stainless steel and titanium/platinum/tungsten alloys. The graft member 4 is made of a biocompatible material, such as expanded polytetrafluoroethylene (ePTFE), polyester fabric, polypropylene, microporous urethane, hexafluoropropylene, polyfluorocarbon, Polyamide, polyethylene terephthalate, nylon, lycra, or other suitable biocompatible material, or alternatively a multilayer liner or compounding material made from one or one more materials.

Figure 8:
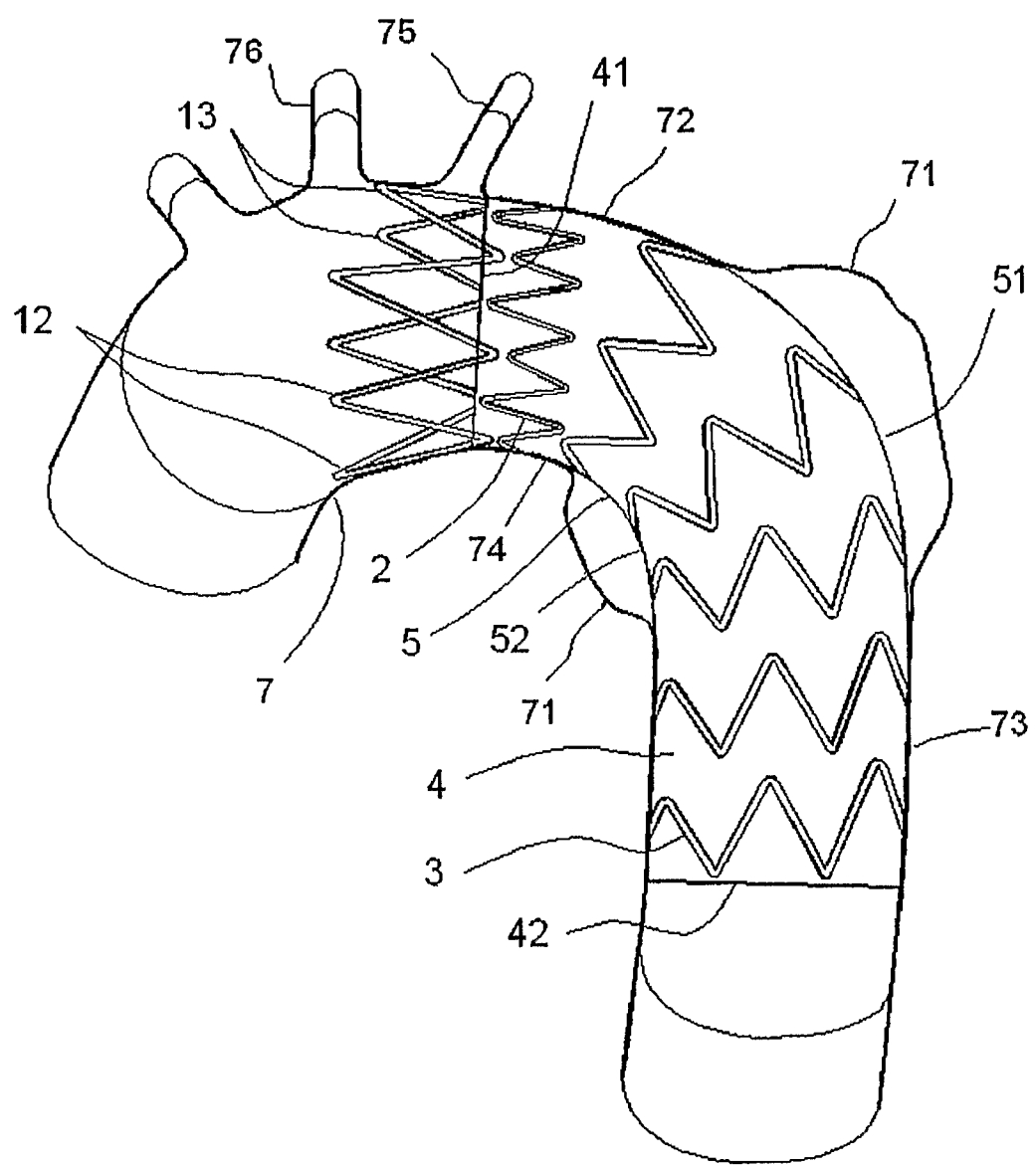
FIG. 8 illustrates the tubular stent graft in use implanted within the aortic arch.

FIG. 8 illustrates the tubular stent graft 5 in use implanted within the aortic arch 7. Prior to deployment, the stent graft 5 is sterilized, disposed within a sheath of a delivery system and then transferred via a delivery system to the diseased area in the aortic arch 7. Before being deployed within the arch 7, the rigid side 51 where the connecting bar 71 lies is positioned towards the outward curve 72 of the arch 7, and the proximal end 41 of the graft member 4 is positioned within the proximal aneurysm neck, close to the distal end of the port of the left subclavian artery 75. During deployment, the open stent member 1 is deployed first. The short wave apexes 13 are sized and dimensioned to avoid covering the branch port of the left normal carotid and the high wave apexes 12 are sized and dimensioned to contact the wall 74 of inward curve of the arch 7 before they overturn.

Next, the mini-wave stent member 2 and the sloping stent members 3 expand and affix themselves to the wall of aorta 7. The stent graft 5 flexes within the arch 7. The rigid side 51 of the stent graft 5 maintains its longitudinal length, while the flexible side 52 shrinks in length because the soft graft member 4 between sloping stent members 3 retracts allowing the two neighboring stent members 3 to move closer. The mini-wave stent member comprises more apexes 21, 22, 23 and undulations than the sloping stent members 3. These additional apexes allow the mini-wave to form more easily to the irregular profile of the inner lumen of the aneurysm neck 72, 74 and affix the stent graft to the wall of the aorta 7. This reduces the potential for proximal endoleakage.

Figure 9:
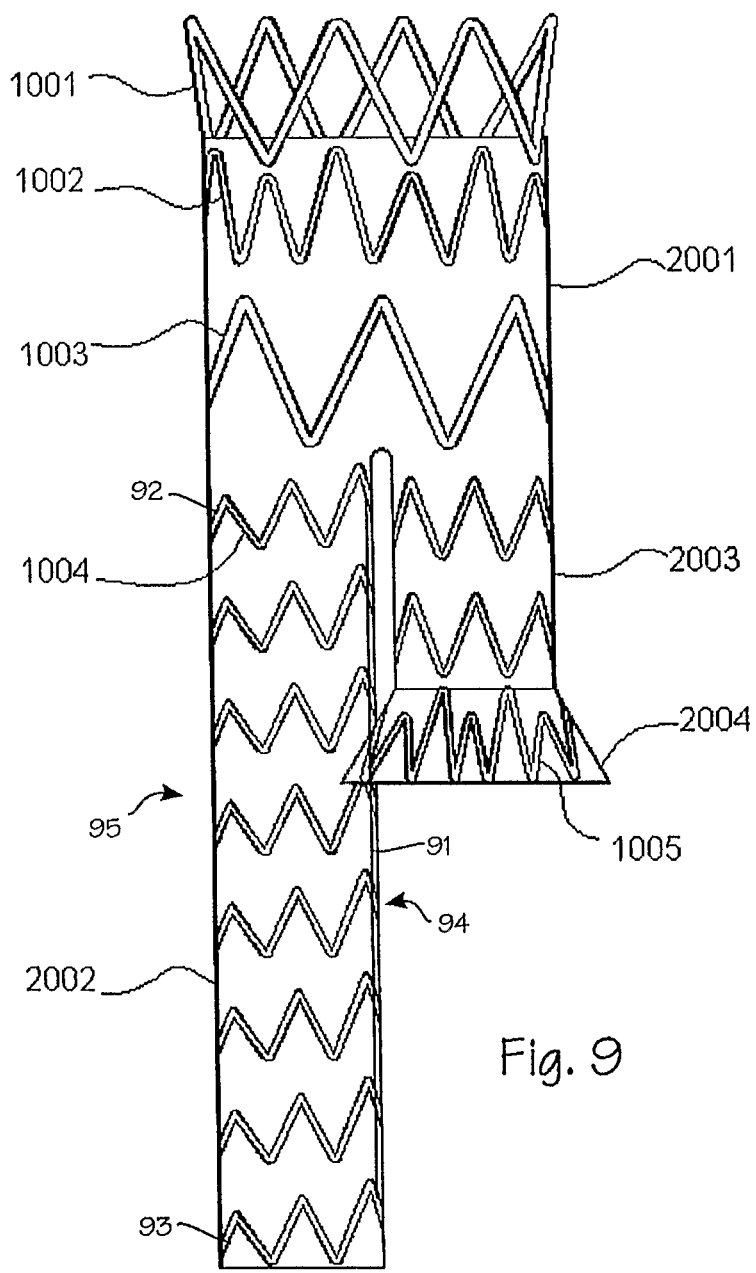
FIG. 9 illustrates a bifurcated stent graft.

FIG. 9 illustrates a bifurcated stent graft. The bifurcated stent graft comprises an open stent member 1001, two mini-wave stent members 1002, 1005, a plurality of sloping stent members 1004 and a plurality of uniform stent members 1003 coupled to a tubular bifurcated graft member 2001. The bifurcated graft member 2001 comprises a trunk graft portion 2001 and two branch portions extending from the distal end of the trunk graft portion. The first branch portion extending from the trunk portion is a long branch graft portion 2002 also referred to as an ipsilateral iliac branch graft portion. The second branch portion is a short branch graft portion 2003 which is referred to as a contralateral iliac branch graft portion.

The short branch graft portion 2003 further comprises an umbrella-like introducing graft portion 2004 disposed on its distal end. The introducing graft portion 2004 is flared or frustoconical in shape having a larger distal outer diameter than the short branch graft portion 2003. The distal apexes of the open stent member 1001 are coupled to the proximal end of the trunk graft portion 2001 of the bifurcated tubular graft member. A mini-wave stent member 1002 is fixed fully to the trunk graft portion 2001 with each high wave apex 22 positioned close to the proximal end of the trunk graft portion 2001 and between the distal apexes of the open stent member 1001. One or more uniform stent members 1003 are coupled to the trunk graft portion 2001 and to the short branch portion 2003. A uniform stent member comprises multiple even undulations and apexes defining a tubular configuration with the proximal apexes or crests lying in substantially the same plane and the distal apexes or troughs lying in substantially the same plane. The uniform stent member has a substantially uniform longitudinal distance or wave height along the uniform stent member.

A plurality of sloping stent members 1004 are coupled to the long branch graft member 2002 in adjacent instances. The sloping stent members are uniformly spaced apart along the long branch graft portion 2002. Each high wave apex 32 is positioned on the same radial side close to the short branch graft portion 2003. The distal end of each sloping stent member 1004 is directed towards the distal end of the long branch graft portion 2002. A longitudinal bar 91 connects the proximal most sloping stent member 92 and the distal most sloping stent member 93 on the rigid side 94 which is the side closest to the short branch graft portion 2003. One or more radiopaque markers may be disposed within said tubular graft member 5.

The stent members, including the open stent member 1001, the mini-wave stent member 1002, 1005, the normal stent members 1003 and the sloping stent member 1004, are made of biocompatible material, such as, not limited to, nitinol, cobalt chrome alloys (e.g. Elgiloy), stainless steel or titanium/platinum/tungsten alloys. The bifurcated tubular graft member 2001 is made of a biocompatible material, such as, not limited to, expanded polytetrafluorethylene (ePTFE), polyester fabric, polypropylene, microporous urethane, hexafluoropropylene, polyfluorocarbon, Polyamide, polyethylene terephthalate, nylon, lycra, or other suitable biocompatible material, or alternatively a multilayer liner or compounding material made of/from one or one more materials previously mentioned.

Figure 10:
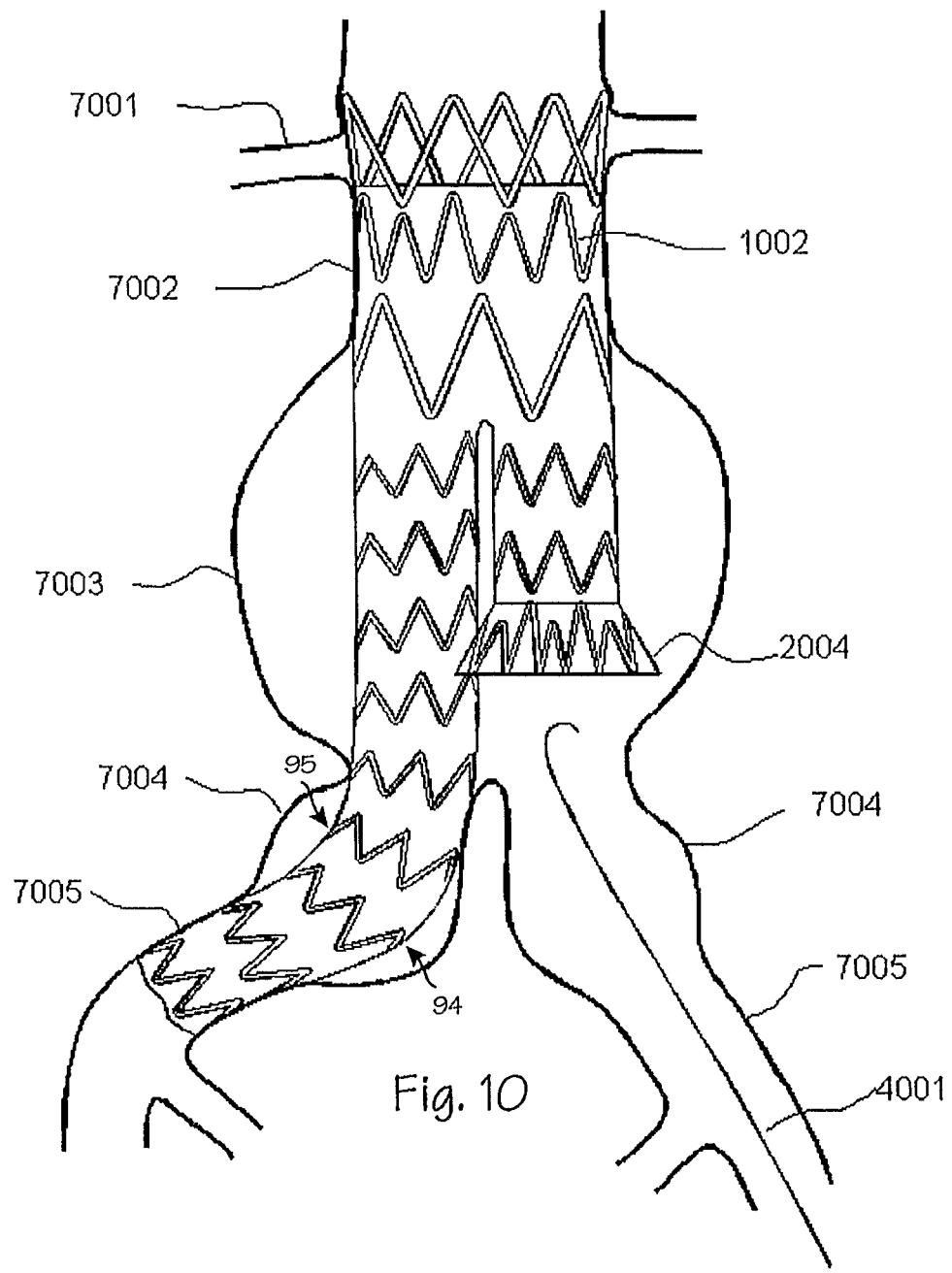
FIG. 10 illustrates the bifurcated stent graft implanted within an abdominal aortic aneurysm.

FIG. 10 illustrates the bifurcated stent graft implanted within an abdominal aortic aneurysm 7003. Prior to implantation, the stent graft is sterilized, disposed within a sheath of a delivery system and then delivered via the delivery system to the diseased area of the vessel in the abdominal aortic aneurysm 7003. During the deployment procedure within the abdominal aorta and ipsilateral iliac artery, the proximal end of the trunk graft portion 2001 is positioned within the proximal aneurysm neck 7002 and close to the distal end of the lower renal artery 7001 opening. The open stent member 1001 is first deployed, covering the renal artery without cutting off the blood flow into the renal artery and facilitating the fixation of the stent graft to the vessel wall. While being deployed, the mini-wave stent member 1002 and the uniform stent member 1003 within the trunk graft portion 2001 expand and affixes the bifurcated stent graft to the neck of the vessel wall 7002. The mini-wave stent member 1005 within the introducing graft portion 2004 expands within the sac of the aneurysm 7003.

Once removed from the deployment sheath, the sloping stent members 1004 within the distal part of the long branch graft portion 2002 expand accordingly and affix themselves to the common iliac artery 7005. The sloping stent members 1004 flex within the curved iliac artery. During deployment, the space between the sloping stent members 1004 retracts along the flexible side 95 of the long branch graft portion 2002 allowing neighboring stent members 1004 to move closer. The mini-wave stent member 1002 comprises more apexes 21, 22, 23 and undulations than the uniform stent members 1003. As a result, the mini-wave stent member 1002 is more capable of forming to the irregular or deformed profile of the inner lumen of the aneurysm neck 7002 and affixing the stent graft to the vessel wall which will reducing the possibility of proximal endoleakage.

While the introducing graft portion 2004 expands, it creates an inner diameter larger than the inner diameter of short graft portion 2003 forming a funnel or conical shape. The conical shape of the introducing graft portion 2004 makes it comparatively easy to center and place the guide wire into the introducing graft portion 2004. Once the guide wire is inside the introducing graft portion 2004, it is easier to then place the guide wire within the short graft portion 2003 when the bifurcated stent graft is disposed within the large aneurysm sac 7003.

Figure 11:
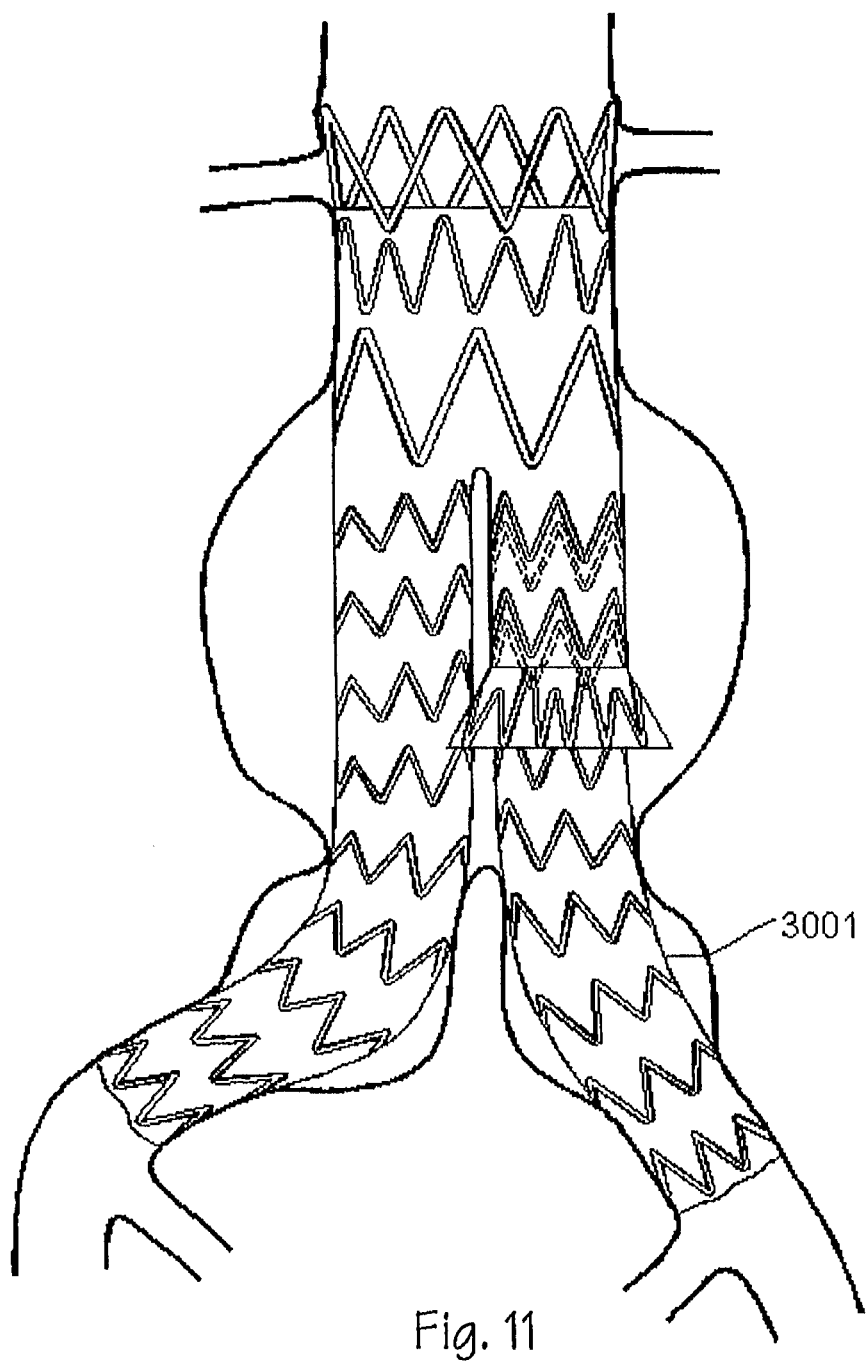
FIG. 11 illustrates the bifurcated stent graft having a branch extension implanted within an abdominal aortic aneurysm.

FIG. 11 illustrates the bifurcated stent graft having a branch extension implanted within an abdominal aortic aneurysm. After the bifurcated stent is initially deployed, a branch extension 3001 is placed within the iliac artery and coupled to the short branch portion. Once implanted, the bifurcated stent graft with the branch extension isolates the diseased portion of the vessel containing the aneurysm from blood pressure within the vessel. Thus, blood flows into the iliac arteries through the stent graft without bringing pressure on the vessel wall within the aneurysm sac.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

The invention claimed is:

1. A stent graft comprising:
a tubular graft member;
a plurality of sloping stent members substantially coaxial with and coupled to the tubular graft member and further characterized by a high wave apex and a low wave apex, said high wave apexes of the plurality of sloping stent members positioned on a same radial side of the stent-graft;
a mini-wave stent member substantially coaxial with and coupled to a proximal section of the graft member, said mini wave stent member comprising multiple undulations and uneven apexes disposed about the longitudinal axis defining a round tubular configuration;
wherein each of the sloping stent members comprise multiple uneven apexes characterizing a round tubular configuration with a distal end and a proximal end disposed about a longitudinal axis; and
wherein the distal apexes of the sloping stent member are arranged in substantially same plane substantially horizontal to the longitudinal axis of the sloping stent member and the proximal apexes are arranged in a sloping plane oblique to the longitudinal axis.

2. The stent graft of claim 1 wherein the sloped stent members are uniformly distributed along the stent graft.

3. The mini-wave stent member of claim 1 comprising a plurality of distal apexes arranged in substantially the same plane substantially horizontal to the longitudinal axis of the mini-wave stent member and a plurality of proximal apexes arranged in two different planes substantially horizontal to the longitudinal axis of the mini-wave stent member providing the mini-wave stent member with two wave heights characterizing a high wave apex and a low wave apex.

4. The stent graft of claim 1 further comprising an open stent member substantially coaxial with and coupled to the proximal end of said graft member, said open stent member comprising multiple undulations and apexes defining a round tubular configuration.

5. The open stent member of claim 4 comprising multiple distal apexes arranged in substantially the same plane substantially horizontal to the longitudinal axis of the open stent member and a plurality of proximal apexes arranged in two different planes substantially horizontal to the longitudinal axis of the open stent member providing the open stent member with two wave heights.

6. The stent graft of claim 1 further comprising a bar connecting a proximal most sloping stent member to a distal most sloping stent member.

7. The stent graft of claim 1 further comprising a bar connecting a sloping stent member to its neighboring sloping stent member.

8. The stent graft of claim 1 wherein the number of apexes in the mini-wave stent member about double the number of apexes found in the sloping stent member.

9. The stent graft of claim 3 wherein one or more high wave apexes are disposed between every two short wave apexes.

10. A stent-graft comprising:
a tubular graft member;
an open stent member with a plurality of uneven apexes, said open stent member substantially coaxial with and coupled to a proximal end of the graft member with the proximal apexes of said open stent member arranged in two or more different planes substantially perpendicular to a longitudinal axis of said open stent member and the distal apexes arranged in substantially the same plane; and
a plurality of a plurality of sloped stent members, said sloped stent members substantially coaxial with and coupled to the tubular graft member;
wherein each of the sloping stent members comprise multiple uneven apexes characterizing a round tubular configuration with a distal end and a proximal end disposed about a longitudinal axis;
wherein the distal apexes of the sloping stent member are arranged in substantially same plane substantially horizontal to the longitudinal axis of the sloping stent member and the proximal apexes are arranged in a sloping plane oblique to the longitudinal axis.

11. The stent-graft of claim 10 further comprising a mini-wave stent member substantially coaxial with and coupled to a proximal section of the graft member, said mini wave stent member comprising multiple undulations and apexes disposed about the longitudinal axis defining a round tubular configuration;
wherein the distal apexes of the mini-wave stent are arranged in substantially the same plane substantially horizontal to a longitudinal axis of the mini-wave stent member and the proximal apexes are arranged in two different planes substantially horizontal to the longitudinal axis of the mini-wave stent member providing the mini-wave stent member with two wave heights characterizing a high wave apex and a low wave apex.

12. A stent-graft comprising:
a tubular graft member; and
a mini-wave stent member substantially coaxial with and coupled to a proximal section of the graft member, said mini wave stent member comprising multiple undulations and apexes disposed about the longitudinal axis defining a round tubular configuration;
wherein the distal apexes of the mini-wave stent are arranged in substantially the same plane substantially horizontal to a longitudinal axis of the mini-wave stent member and the proximal apexes are arranged in two different planes substantially horizontal to the longitudinal axis of the mini-wave stent member providing the mini-wave stent member with two wave heights characterizing a high wave apex and a low wave apex.

13. The stent-graft of claim 12 further comprising a plurality of sloped stent members, said sloped stent members substantially coaxial with and coupled to the tubular graft member;
wherein each of the sloping stent members comprise multiple uneven apexes characterizing a round tubular configuration with a distal end and a proximal end disposed about a longitudinal axis; and
wherein the distal apexes of the sloping stent member are arranged in substantially same plane substantially horizontal to the longitudinal axis of the sloping stent member and the proximal apexes are arranged in a sloping plane oblique to the longitudinal axis.

14. A stent graft comprising:
a tubular graft member;
a plurality of sloping stent members substantially coaxial with and coupled to the tubular graft member;
a mini-wave stent member substantially coaxial with and coupled to a proximal section of the graft member, said mini wave stent member comprising multiple undulations and uneven apexes disposed about the longitudinal axis defining a round tubular configuration, the mini-wave stent member further comprising a plurality of distal apexes arranged in substantially the same plane substantially horizontal to the longitudinal axis of the mini-wave stent member and a plurality of proximal apexes arranged in two different planes substantially horizontal to the longitudinal axis of the mini-wave stent member providing the mini-wave stent member with two wave heights characterizing a high wave apex and a low wave apex;
wherein each of the sloping stent members comprise multiple uneven apexes characterizing a round tubular configuration with a distal end and a proximal end disposed about a longitudinal axis; and
wherein the distal apexes of the sloping stent member are arranged in substantially same plane substantially horizontal to the longitudinal axis of the sloping stent member and the proximal apexes are arranged in a sloping plane oblique to the longitudinal axis.

15. The stent graft of claim 14 wherein the sloped stent members are uniformly distributed along the stent graft.

16. The stent graft of claim 15 further comprising an open stent member substantially coaxial with and coupled to the proximal end of said graft member, said open stent member comprising multiple undulations and apexes defining a round tubular configuration.

17. The open stent member of claim 15 comprising multiple distal apexes arranged in substantially the same plane substantially horizontal to the longitudinal axis of the open stent member and a plurality of proximal apexes arranged in two different planes substantially horizontal to the longitudinal axis of the open stent member providing the open stent member with two wave heights.

18. The stent graft of claim 15 further comprising a bar connecting a proximal most sloping stent member to a distal most sloping stent member.

19. The stent graft of claim 14 further comprising a bar connecting a sloping stent member to its neighboring sloping stent member.

20. The stent graft of claim 14 wherein the number of apexes in the mini-wave stent member about double the number of apexes found in the sloping stent member.

21. The stent graft of claim 14 wherein one or more high wave apexes are disposed between every two short wave apexes.

22. A stent graft comprising:
a tubular graft member;
a plurality of sloping stent members substantially coaxial with and coupled to the tubular graft member;
a mini-wave stent member substantially coaxial with and coupled to a proximal section of the graft member, said mini wave stent member comprising multiple undulations and uneven apexes disposed about the longitudinal axis defining a round tubular configuration; and
an open stent member substantially coaxial with and coupled to the proximal end of said graft member, said open stent member comprising multiple undulations and apexes defining a round tubular configuration the open stent member comprising multiple distal apexes arranged in substantially the same plane substantially horizontal to the longitudinal axis of the open stent member and a plurality of proximal apexes arranged in two different planes substantially horizontal to the longitudinal axis of the open stent member providing the open stent member with two wave heights;
wherein each of the sloping stent members comprise multiple uneven apexes characterizing a round tubular configuration with a distal end and a proximal end disposed about a longitudinal axis;
wherein the distal apexes of the sloping stent member are arranged in substantially same plane substantially horizontal to the longitudinal axis of the sloping stent member and the proximal apexes are arranged in a sloping plane oblique to the longitudinal axis.

23. The stent graft of claim 22 wherein the sloped stent members are uniformly distributed along the stent graft.

24. The stent graft of claim 22 further comprising a bar connecting a proximal most sloping stent member to a distal most sloping stent member.

25. The stent graft of claim 23 further comprising a bar connecting a sloping stent member to its neighboring sloping stent member.

26. The stent graft of claim 23 wherein the number of apexes in the mini-wave stent member about double the number of apexes found in the sloping stent member.

27. The stent graft of claim 22 wherein one or more high wave apexes are disposed between every two short wave apexes.

28. A stent graft comprising:
a tubular graft member;
a plurality of sloping stent members substantially coaxial with and coupled to the tubular graft member;
a mini-wave stent member substantially coaxial with and coupled to a proximal section of the graft member, said mini wave stent member comprising multiple undulations and uneven apexes disposed about the longitudinal axis defining a round tubular configuration; and
a bar connecting a sloping stent member to its neighboring sloping stent member;
wherein each of the sloping stent members comprise multiple uneven apexes characterizing a round tubular configuration with a distal end and a proximal end disposed about a longitudinal axis;
wherein the distal apexes of the sloping stent member are arranged in substantially same plane substantially horizontal to the longitudinal axis of the sloping stent member and the proximal apexes are arranged in a sloping plane oblique to the longitudinal axis.

29. The stent graft of claim 28 wherein the sloped stent members are uniformly distributed along the stent graft.

30. The stent graft of claim 28 further comprising a bar connecting a proximal most sloping stent member to a distal most sloping stent member.

31. The stent graft of claim 29 further comprising a bar connecting a sloping stent member to its neighboring sloping stent member.

32. The stent graft of claim 29 wherein the number of apexes in the mini-wave stent member about double the number of apexes found in the sloping stent member.

33. The stent graft of claim 28 wherein one or more high wave apexes are disposed between every two short wave apexes.

* * * * *